US00PP16534P2

(12) United States Plant Patent
Trees

(10) Patent No.: US PP16,534 P2
(45) Date of Patent: May 16, 2006

(54) ***GERANIUM* PLANT NAMED 'BALFANERO'**

(50) Latin Name: *Pelargonium×hortorum*
Varietal Denomination: Balfanero

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 114 days.

(21) Appl. No.: 11/015,431

(22) Filed: Dec. 17, 2004

(51) Int. Cl.
*A01H 5/00* (2006.01)

(52) U.S. Cl. ..... Plt./328
(58) Field of Classification Search ..... Plt./328
See application file for complete search history.

(56) References Cited

U.S. PATENT DOCUMENTS

PP11,767 P2 * 2/2001 Trees ..... Plt./328

OTHER PUBLICATIONS

UPOV ROM GTITM Computer Database, GTI Jouve Retrieval Software 2005/02 Citation for 'Balfanero'.*

* cited by examiner

*Primary Examiner*—Kent Bell
*Assistant Examiner*—W. C. Haas
(74) *Attorney, Agent, or Firm*—Wood, Phillips, Katz, Clark & Mortimer

(57) ABSTRACT

A new and distinct cultivar of *Geranium* plant named 'Balfanero', characterized by its semi-double hot pink-colored flowers, dark green-colored foliage, and vigorous, upright,t and mounded growth habit.

1 Drawing Sheet

Latin name of genus and species of plant claimed: *Pelargonium×hortorum.*
Variety denomination: 'Balfanero'.

BACKGROUND OF THE INVENTION

The present invention relates to a new and distinct cultivar of *Geranium* plant botanically known as *Pelargonium× hortorum* and hereinafter referred to by the cultivar name 'Balfanero'.

The new cultivar originated in a controlled breeding program in Arroyo Grande, Calif., during February 2000. The objective of the breeding program was the development of *Geranium* cultivars with a vigorous, upright mounded growth habit, dark green-colored foliage, and new and unique flower color.

The female (seed) parent of the new cultivar was the proprietary breeding line 855-10, not patented, characterized by its semi-double hot pink-colored flowers, dark green-colored foliage, and medium growth habit. The male (pollen) parent of the new cultivar was the proprietary breeding line 1090-1, not patented, characterized by its large semi-double hot pink-colored flowers, dark green-colored foliage, and medium growth habit. The new *Geranium* was discovered and selected by the inventor as a single flowering plant within the progeny of the above stated cross-pollination during March 2001 at Arroyo Grande, Calif.

Asexual reproduction of the new cultivar by terminal stem cuttings since March 2001 at Arroyo Grande, Calif. and West Chicago, Ill., has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balfanero' as a new and distinct cultivar of *Geranium* plant:

1. Semi-double hot pink-colored flowers.
2. Dark green-colored foliage.
3. Vigorous, upright, and mounded growth habit.

Plants of the new cultivar differ from plants of the female parent primarily in plant vigor and from plants of the male parent primarily in plant vigor.

Of the many commercially available *Geranium* cultivars known to the inventor, the most similar in comparison to the new cultivar is 'Balfanfaro', U.S. Plant Pat. No. 11,767. However, in side by side comparisons, plants of the new cultivar differed from plants of 'Balfanfaro' in the following characteristics:

1. Plants of the new cultivar exhibit lighter flower color than plants of 'Balfanfaro'.
2. Plants of the new cultivar exhibit fewer flowers per umbel than plants of 'Balfanfaro'.
3. Plants of the new cultivar have shorter pedicels than plants of 'Balfanfaro'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balfanfaro'. The plants were grown for 8 weeks in a greenhouse at West Chicago, Ill.

DETAILED BOTANICAL DESCRIPTION

Figure 1:
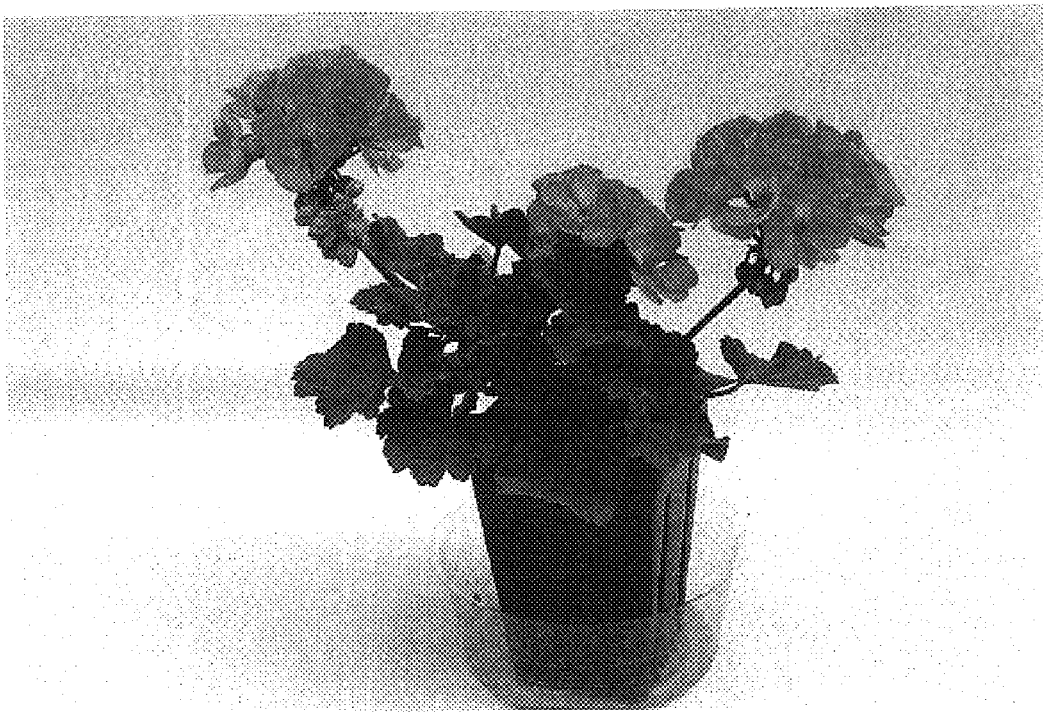
FIG. 1 illustrates a side view of the overall growth and flowering habit of 'Balfanero'.
Figure 2:
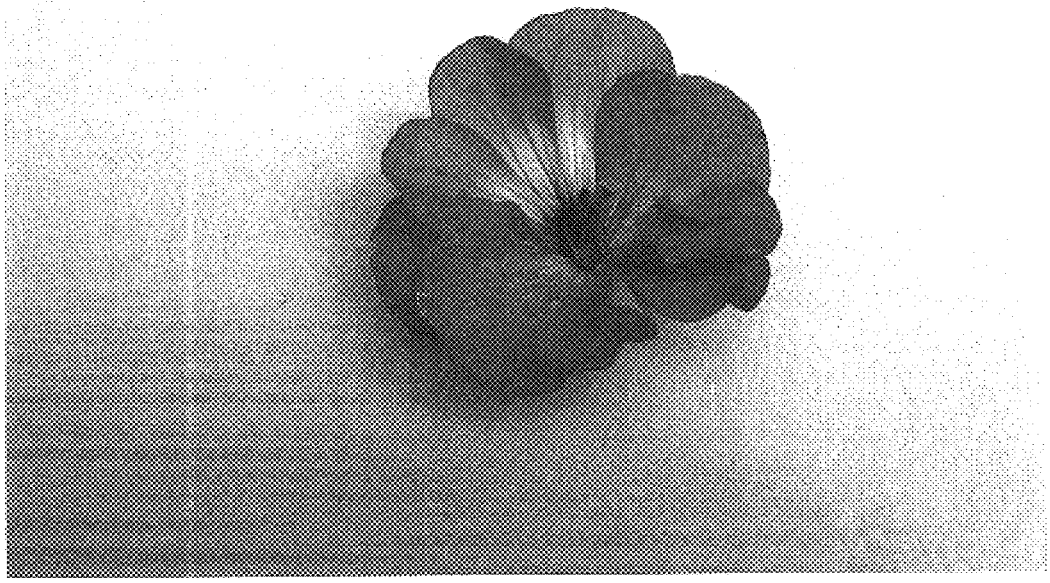
FIG. 2 illustrates a close-up view of a single flower of 'Balfanero'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Oct. 9, 2004 between 10:00 and 11:45 a.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 8 weeks utilizing a soilless growth medium. Greenhouse temperatures were maintained at approximately 65° F. to 70° F. (18° C. to 21° C.) during the day and approximately 60° F. to 65° F. (15° C. to 18° C.) during the night. Greenhouse light levels of 4,000–6,000 footcandles were maintained during the day.

Botanical classification: *Pelargonium×hortorum* cultivar Balfanero.

Parentage:

*Female parent.*—Proprietary breeding line 855-10, not patented.

*Male parent.*—Proprietary breeding line 1090-1, not patented.

Propagation:

*Type cutting.*—Terminal stem.

*Time to initiate roots.*—Approximately 10 to 14 days.

*Time to produce a rooted cutting.*—Approximately 21 to 28 days.

*Root description.*—Fibrous.

*Rooting habit.*—Freely branching.

Plant description:

*Crop time.*—Approximately 8 to 9 weeks from planting of rooted cutting to finish.

*Growth habit and general appearance.*—Vigorous, upright, and mounded.

*Height from soil level to top of plant plane.*—Approximately 18.7 cm.

*Width/area of spread.*—Approximately 25.9 cm.

*Branching habit.*—Freely basal branching. Approximately 2 branches per plant.

*Branch description.*—Length: Approximately 5.2 cm. Diameter: Approximately 6.7 mm. Texture: Hirsute Dense short, soft. Color: 138A. Internode length at center of branch: Approximately 6.4 mm.

*Foliage description.*—Number of leaves per lateral branch: Approximately 13. Form: Mature foliage is simple. Arrangement: Opposite. Shape: Reniform. Margin: Crenate. Apex: Rounded. Base: Cordate, open. Venation pattern: Palmate. Length of mature leaf: Approximately 4.4 cm. Width of mature leaf: Approximately 7.2 cm. Upper surface texture: Densely pubescent. Lower surface texture: Densely pubescent especially along veins. Color of upper surface of mature foliage: Darker than 147A with venation of 146A and zone at inner ⅓ of leaf of 147A. Color of lower surface of mature foliage: Darker than 147B with venation of 146A. Petiole length: Approximately 7.4 cm. Petiole diameter: Approximately 2.2 mm. Petiole Texture: Pubescent on both upper and lower surface. Petiole color: 146A.

Flowering description:

*Flowering habit.*—'Balfanero' is freely flowering under outdoor growing conditions with substantially continuous blooming from spring through autumn and year round under greenhouse conditions.

*Time to first flower.*—Approximately 8 weeks after planting of rooted cutting.

*Lastingness of individual bloom.*—Approximately 5 to 7 days.

Inflorescence description:

*Type.*—Hemisperical umbel. Position: Above foliage. Number of open umbels at any one time: 3. Number of developing umbels at any one time: 2. Umbel diameter: Approximately 9.1 cm. Umbel height/depth: Approximately 5 cm. Number of flowers per umbel: Approximately 14.

*Peduncle.*—Strong, erect. Length: Approximately 14.1 cm. Diameter: Approximately 3.4 mm. Texture: Densely pubescent. Color: 144A.

Flower description:

*Bud rate of opening.*—Generally takes 3 to 5 days for bud to progress from first color to fully open flower.

*Bud just before opening.*—Shape: Round. Length: Approximately 1.1 cm. Diameter: Approximately 7.1 mm. Texture of sepals: Densely pubescent. Texture of petals: Glabrous. Petal color: 65A. Sepal color: 143A with overlay of 187A.

*Corolla.*—Form: Semi-double. Shape: Round, slightly cupped. Diameter/Width: Approximately 4.9 cm. Depth: Approximately 1.7 cm. Fragrance: None. Persistent.

*Petals/petaloids.*—Quantity: Approximately 8 petals and 4 irregular shaped petaloids per flower. Arrangement: Imbricate. Shape: Obovate. Apex: Obtuse. Base: Attenuate. Margin: Entire. Texture of upper and lower surface: Glabrous. Upper petal length: Approximately 2.6 cm. Upper petal width: Approximately 2.1 cm. Lower petal length: Approximately 2.7 cm. Lower petal width: Approximately 2.2 cm. Color of upper surface of fully open upper petals and petaloids: 67B with base of 65B and venation of 67A. Color of upper surface of lower petals and petaloids: 67A. Color of lower surface of fully open upper petals and petaloids: 65A with 68B at margin and venation of N66C. Color of lower surface of fully open lower petals and petaloids: 65A with 68B at margin.

*Pedicel.*—Strength: Strong. Angle: Acute. Length: Approximately 3.9 cm. Diameter: Approximately 1.5 mm. Texture: Soft, short dense hairs. Color: 144B with overlay of 187C.

*Sepals.*—Quantity of sepals per flower: 5. Sepal shape: Lanceolate. Sepal apex: Acuminate. Sepal base: Truncate. Sepal margin: Entire. Sepal length: 1.1 cm. Sepal width: 3.2 mm. Sepal texture: Upper/inner surface: Glabrous. Lower/outer surface: Densely pubescent. Color of upper and lower surface: 187A with tip of 143A.

*Reproductive organs.*—Androecium: Quantity of mature anthers: Approximately 5. Anther length: Approximately 2 mm. Mature anther color: 64B. Pollen amount: Moderate. Pollen color: 31A. Gynoecium: Pistil quantity: One per flower. Pistil length: Approximately 1.3 cm. Stigma shape: 5 pointed star. Stigma length: 3 mm. Stigma color: 64B. Style length: 3 mm. Style color: 64B. Ovary length: 7 mm. Ovary diameter: 2 mm. Ovary texture: Sericeous. Ovary color: 143B with overlay of 187A.

Seed and fruit production: Neither seed nor fruit production has been observed.

Disease and pest resistance: Resistance to pathogens and pests common to *geraniums* has not been observed.

What is claimed is:

1. A new and distinct cultivar of *Geranium* plant named 'Belfanero', substantially as herein shown and described.

* * * * *